United States Patent [19]

Schiessl

[11] Patent Number: 5,015,355
[45] Date of Patent: May 14, 1991

[54] CORROSION MEASURING CELL

[75] Inventor: Peter Schiessl, Aachen, Fed. Rep. of Germany

[73] Assignee: Strabag Bau-AG, Koeln-Deutz, Fed. Rep. of Germany

[21] Appl. No.: 418,555

[22] Filed: Oct. 10, 1989

[30] Foreign Application Priority Data

Oct. 11, 1988 [DE] Fed. Rep. of Germany ....... 3834628

[51] Int. Cl.$^5$ ............................................. G01N 17/02
[52] U.S. Cl. ..................................... 204/404; 204/412
[58] Field of Search ................... 204/153.11, 404, 412; 324/65 CR, 71.2

[56] References Cited

U.S. PATENT DOCUMENTS

| 2,947,679 | 8/1960 | Schaschl et al. | 204/404 |
| 3,197,388 | 7/1965 | Marsh et al. | 204/404 X |
| 4,703,255 | 10/1987 | Strommen | 204/153.11 X |

FOREIGN PATENT DOCUMENTS

| 0259253 | 8/1987 | European Pat. Off. |
| 2335419 | 2/1975 | Fed. Rep. of Germany. |
| 3531478 | 3/1987 | Fed. Rep. of Germany. |
| 3531479 | 3/1987 | Fed. Rep. of Germany. |
| 72398 | 2/1975 | German Democratic Rep. |

OTHER PUBLICATIONS

DE-2 Galvanotechnik 68, 1977, No. 3 2.351–355, insbes. 2. 352, rechte Spalte.
JP 54 86444, In: Patents Abstracts of Japan, C-58, Sep. 12, 1979, vol. 3, No. 109.

Primary Examiner—Nam X. Nguyen
Attorney, Agent, or Firm—Body, Vickers & Daniels

[57] ABSTRACT

A corrosion measuring cell for establishing the start of corrosion and/or for measuring the degree of corrosion of structural or reinforcing steel, which is embedded in a concrete structural part, has a corrosion-resistant cathode electrode, and several ordinary steel anode electrodes spaced from one another at different distances from the external surface of the concrete structural part.

The anode electrodes are each connected to a cathode electrode through a current-measuring device which measures current due to corrosion at the anodes in order to establish the temporal course of carbonatization or chloridization taking place in the concrete. The connections may be switched between the measuring device and a polarizing device which polarizes the anode electrode in such a manner that the corrosion current, and thus the corrosion of the anode electrode, stops when desired to avoid damage to the concrete.

28 Claims, 5 Drawing Sheets

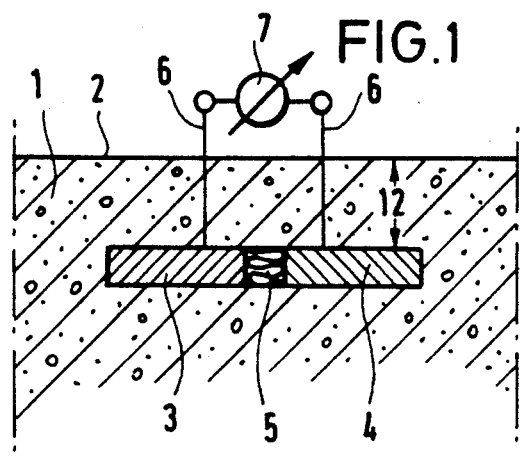

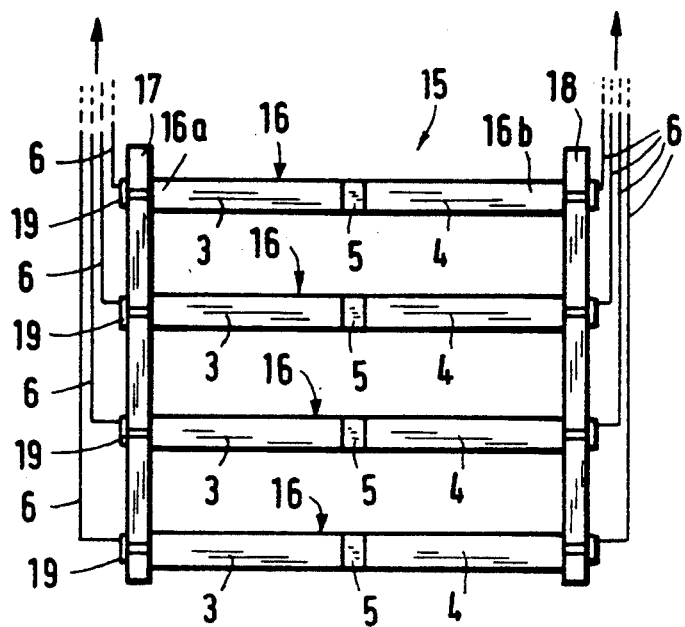
FIG.4
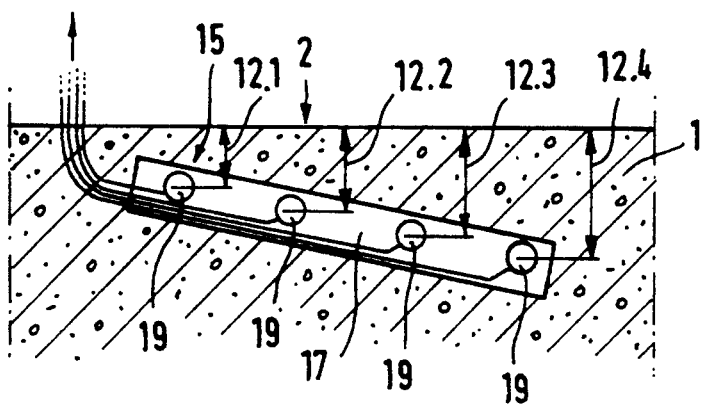
FIG.5
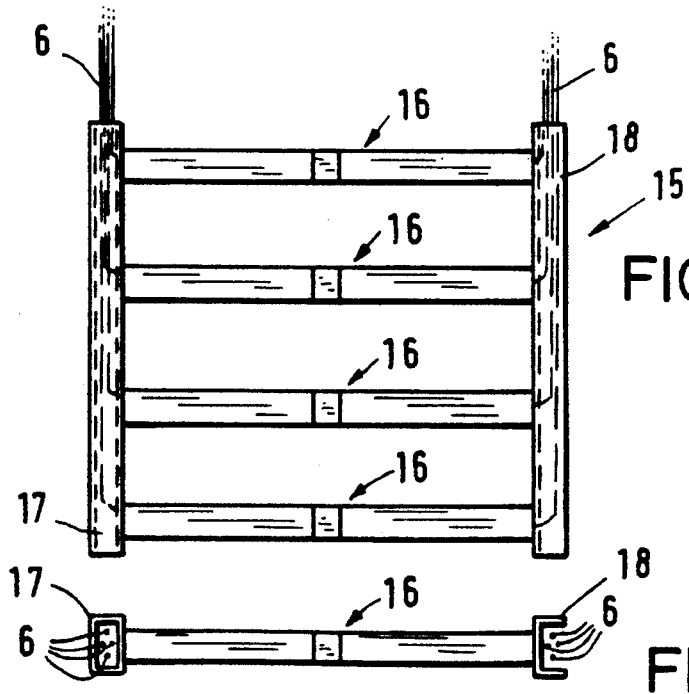
FIG.6
FIG.7

CORROSION MEASURING CELL

FIELD OF THE INVENTION

The invention relates to a corrosion measuring cell for establishing the start of corrosion and/or for measuring the degree of corrosion of structural or reinforcing steel, which is embedded in a concrete structural part, with at least two electrodes, which are arranged in this concrete structural part at a distance from one another and one of which consists of conventional structural or reinforcing steel and the other of a more noble metal, which is also protected against corrosion in a concrete which is carbonatized or contains chlorides, the electrodes being electrically connected via a measuring element, which is accessible from the outside and detects the appearance and/or the size of an electric current which arises between the electrodes in the event of corrosion of the structural or the reinforcing steel electrode starting.

BACKGROUND OF THE INVENTION

Steel parts, which are embedded in concrete, such as sectional steel girders or reinforcing inserts made of steel, are, in a concrete which is composed and worked in accordance with regulations, generally permanently protected against corrosion under a sufficiently thick concrete covering. This protection against corrosion does not depend upon the impermeability of the concrete, but on the alkalinity of the concrete interstitial water, which usually has a pH value $> 12.5$. Under these conditions, on the surface of the steel, a thin firmly adherent oxide layer is formed, which practically completely prevents corrosion. Only in this way does reinforced concrete become usable for external structural parts, which are exposed to weathering.

Under certain unfavourable conditions, however, the protection against corrosion of the concrete can be lost. Errors in construction as well as especially unfavourable environmental conditions are examples of such conditions.

The cause of the corrosion may be carbonatization of the concrete, which takes place when carbon dioxide from the air reacts with the alkaline components of the cement. As a result of such a chemical reaction, the pH value falls and the protection against corrosion is lost. Another cause of corrosion is the penetration of chlorides into the concrete, which can happen if, for example, de-icing salts are spread on the concrete roadway of a bridge, which then penetrate in solution into the inside of the concrete member. Both processes begin on the surface of the concrete and continue into the inside of the concrete to the steel parts embedded there, where they cause the oxide layer adhering to the latter to disappear. On the surface of the steel, a critical state is then reached, in which corrosion sets in on the steel parts, without this being discernible at first on the surface of the concrete. Corrosion damage only becomes discernible when the corrosion of the steel is already relatively well advanced and the concrete covering spalls because of the explosive pressure of the rust products. Generally the corrosion is by then so far advanced that very costly and expensive repair measures become necessary. In many cases, a repair is often no longer even possible, so that the structure has to be demolished and replaced with a new one. The extent of damage caused by corrosion of the reinforcement in reinforced concrete and prestressed concrete structures is relatively great. In roadbridge construction the repair work necessary each year today costs more than 1% of the replacement costs of the building material.

DISCUSSION OF THE PRIOR ART

For the non-destructive monitoring of the corrosion of steel parts in concrete it is known to embed probes in the concrete, at a distance from the surface of the concrete, which are connected to a measuring element arranged outside the concrete structural part (DE 35 31 478 A1 and DE 35 31 479 A1). The probes consist of two electrodes, one of which consists of the same material as the supporting steel parts or reinforcing inserts, which are embedded in the concrete, and the other of which is manufactured either from another corrosion-resistant metal, copper for example, or also from reinforcing steel, this other reinforcing steel electrode, however, then being surrounded with an electrically conductive protective covering, which prevents corrosion of this other reinforcing steel electrode. Both electrodes are connected to one another via a measuring element by means of conductors, so that at the moment when the active electrode, which consists of reinforcing steel and lies unprotected in the concrete, starts to corrode, for example when chlorides penetrating from the surface of the concrete have destroyed its protective oxide layer, an electric current arises and can be measured in the measuring element. The electric current, which indicates the start of corrosion, is brought about by virtue of copper having a higher potential than conventional reinforcing steel in the electrochemical series. The result of this is that, in an electrolytic solution, the copper acts as a cathode and the base reinforcing steel becomes the anode. Even with an external electrical connection between a corroding structural steel anode and a corrosion-resistant structural steel cathode, the iron dissolution takes place at the anode only, while only the formation of hydroxyl ions takes place at the cathode. The corrosion process takes place when both electrodes are connected on the one hand electrically conductively via an electrically conductive connection and on the other electrolytically via an electrolyte. The result of the corrosion process is that electrons flow from the anode to the cathode, that is to say during the corrosion process an electric current flows, which is also accessible to measurement.

With the known probes it is only possible to detect a single zone in the concrete structural part, in which the corroding electrode of the probe lies. The appearance of an electric current in the measuring element can thus only provide information as to whether there is danger of corrosion in the zone of the corroding electrode. How quickly carbonatization of the concrete is advancing and when a danger of corrosion for the supporting steel parts, which are embedded in the concrete, will arise cannot, however, be established with the known probes. Moreover these themselves constitute a danger for the structure since they can destroy the concrete as soon as they start to rust like the steel parts which they are intended to monitor.

SUMMARY OF THE INVENTION

The object of the invention is therefore to produce a corrosion measuring cell, of the type more closely described in the introduction, with which the reduction in the alkalinity of the concrete, which takes place from the surface towards the inside of a concrete structure, as a result of carbonatization or chloridization and the associated danger of corrosion for the steel parts embedded in the concrete, can be easily monitored and determined. The object of the invention is also to design the corrosion measuring cell in such a manner that it can be simply built into a concrete structural part, itself causes no destruction of the concrete and also remains usable for any length of time, if it is for a long time in an area exposed to corrosion.

This object is achieved according to the invention in that several electrodes consisting of structural steel or reinforcing steel are arranged at different distances from the external surface of the concrete structural part and that each of these electrodes is connected to the electrode functioning as a cathode, e.g. by being of more noble material, via a measuring element.

A "more noble" material is to be understood as any material which is suitable for the manufacture of an electrode and has a higher potential than conventional reinforcing steel or structural steel in the electrochemical series. Examples of such a more noble material are silver, copper and special steel. Electrodes manufactured from such more noble materials are more generally described below as "cathode electrodes", irrespective of whether they are manufactured from special steel, copper, silver or another material which has a higher potential in comparison with conventional corroding structural steels or reinforcing steels. Steels of all types, such as sectional steels, reinforcing steels or pre-stressing steels, which are worked together with concrete into reinforced concrete, prestressed concrete or composite structural members and are at least partially embedded in the concrete, are generally described below as "structural steels", and the electrodes manufactured from such a steel are called "anode electrodes".

Corrosion measuring cells which according to the invention are provided with several anode electrodes, arranged at different distances from the external surface of the concrete structural part, and several measuring elements assigned to these, make it possible to follow the temporal course of the carbonatization or chloridization of the concrete, which advances towards the inside from the concrete surface of a structure, and to introduce protective measures in good time when the danger of corrosion approaches the supporting steel parts embedded in the concrete. Monitoring of the temporal course of possible damage is especially important because the carbonatization processes do not take place continually and are very dependent upon environmental influences. It is for example entirely possible that carbonatization or chloridization, which at first sets in and stops by itself, is however subsequently restarted and continues. It is also important to recognize whether reconstructive measures which have been introduced have been effective, that is to say whether a sealing of the external surface of the concrete to restrict the access of moisture has resulted in stopping chloridization which is already in process.

In order to inspect the conditions in different levels of a concrete structure it is sufficient to arrange in these horizons anode electrodes which interact with a cathode electrode, which is arranged in an upper horizon and is only separated from the surface of the concrete by a necessary concrete covering. It is particularly expedient however if each anode electrode is assigned a cathode electrode, and each pair of electrodes is arranged at a different distance from the external surface of the concrete structural part and provided with its own measuring element. In each case, in this connection, an anode electrode, a cathode electrode and an insulating piece arranged between the electrodes can be connected to one another to form a one-piece probe element and connected to electrical conductors which are run to the external surface of the concrete structural part. This design makes possible simple installation even in complicated structural parts which contain a large amount of reinforcement.

It is particularly preferred to join the anode electrodes and the cathode electrodes, or the probe elements constituted by the electrodes and insulating pieces, together into a single component, for example by connecting the individual electrodes or pairs of electrodes at a mutual distance from one another at their ends with long shafts, which are made from a material, for example plastic, which does not conduct electric current. The electrical conducting wires, which are connected to the electrodes and which run to the surface of the concrete, can then be fastened to the shafts of the component, which has the approximate shape of a rung ladder, the rungs of which consist of the cathode electrode and the anode electrodes or the anode-cathode pairs, which are mutually insulated, and the shafts of which are e.g. rectangular or profiled rods of insulating material. These components can be built into the concrete with a slight inclination in relation to the surface of the concrete in such a manner that the electrodes, in their longitudinal direction, run approximately parallel to the surface of the concrete, but are at different distances from the latter. The individual electrodes or pairs of electrodes are then at different distances from the surface, which can be selected as required by means of the inclination of the component in relation to the surface of the concrete. Furthermore, such a component in the form of a rung ladder has the advantage that the electrodes or pairs of electrodes, which are arranged at different heights, are independent of and uninfluenced by one another. When fresh concrete is introduced into the shell of the structure which is to be monitored with the corrosion measuring cell, the concrete can flow between the electrodes or pairs of electrodes of the component, which has been positioned in the shell, so that this introduction of fresh concrete is not hindered. Additionally, it is not to be feared that, at the interfaces between component and concrete, paths will be formed along which chlorides can penetrate particularly easily into the inside of the concrete structural member.

In order to protect the electrical wires, which are connected to the electrodes, each shaft may have at least one cavity which runs in the longitudinal direction of the shaft and in which the electrical conductors are accommodated.

On installation of corrosion measuring cells in concrete structures, the problem exists that after the start of any individual measuring cell, that is to say after the corrosion and the associated corrosion current have begun, the anode electrodes corrode. This corrosion can, in particular in the case of anode electrodes arranged in the vicinity of the surface of the concrete, lead to cracks in the concrete and to the spalling of concrete parts on the surface of the concrete as a result of the explosive effect of the rust which is forming. The respective individual measuring cells thus become unusable. Moreover, the concrete of the structure is damaged. By switching off the respective probe element, that is to say by breaking the electrical connection between anode and cathode, the corrosion of the anode electrode cannot be prevented either, since the reinforcing steel of the anode electrode, after the start of the individual element, is in a concrete environment which no longer affords any protection against corrosion. Furthermore, the measuring result of the individual measuring cell is negatively influenced by the increasing corrosion at the anode electrode.

In order to overcome these difficulties, it is preferred to assign to at least that anode electrode which lies closest to a surface of the concrete, a polarizing device on which the corrosion current which arises upon corrosion of the anode electrode can be switched over and which polarizes the anode electrode in such a manner that the corrosion current, and thus the corrosion of the anode electrode, stops.

Desirably, the polarization of the anode electrode is effected by the introduction of external current according to the principle of cathodic corrosion protection. By means of an external current source (battery or galvanostat) an electric current is thus produced from the cathode electrode to the anode electrode. As a result, the anode electrode is protected against further corrosion, while the cathode electrode, as a noble metal, as before does not corrode.

Such a design has the advantage that the respective individual measuring cell can be "shut down", if corrosion has started and a continuing measurement of the corrosion current is not necessary. Although the reinforcing steel of the anode electrode is now in a corrosive environment, further corrosion of the anode electrode, which consists of reinforcing steel or structural steel, can from now on be prevented by means of the introduction of external current and, as a result, damage to the concrete which could arise as a result of corrosion of this anode electrode can be avoided.

It is particularly expedient if the polarizing device is connected in parallel to the respective measuring cell and the corrosion current is optionally switchable, by means of a selective switch, to the measuring cell and the polarizing device. It is thus possible to switch the measuring element of the respective anode electrode or of the respective probe element on again at any time to establish the corrosion current which arises at that time, which is a measure for the degree of corrosion at the respective time and permits conclusions to be drawn with regard to the corrosion danger. By means of shutting down the probe elements, which have become surrounded by a corrosive environment, it is furthermore avoided that individual elements, as a result of corrosion, provide only an imprecise measuring result. Moreover, the individual probe elements produce no corrosion products, which could lead to cracks in the concrete. The corrosion measuring cell and its individual elements thus remain usable over any length of time.

To shut down the individual probe elements, galvanostatic polarizing circuits of known type can, for example, be used. It is particularly expedient, however, if the polarizing device has a potentiostat which polarizes the anode electrode made of reinforcing steel in such a manner that the corrosion current stops.

BRIEF DESCRIPTION OF THE DRAWINGS

Further features and advantages of the invention emerge from the description below and the drawings, in which several embodiments of the invention are described more closely using examples. In the drawings, FIG. 1 shows a schematic representation of an individual measuring cell for a corrosion measuring cell according to the invention, FIG. 2 shows a schematic sectional representation of a first embodiment of the invention, FIG. 4 shows a view from above of pairs of electrodes, joined together into a single component, for a third embodiment of the corrosion measuring cell according to the invention, FIG. 5 shows a lateral view of the corrosion measuring cell according to FIG. 4 built into a concrete structural part, FIG. 6 shows a view from above of a modified embodiment of a component, composed of several pairs of electrodes, for a corrosion measuring cell according to the invention, FIG. 7 shows a front view of the subject of FIG. 6.

DETAILED DESCRIPTION OF THE PREFERRED EMBODIMENTS

Figure 3:
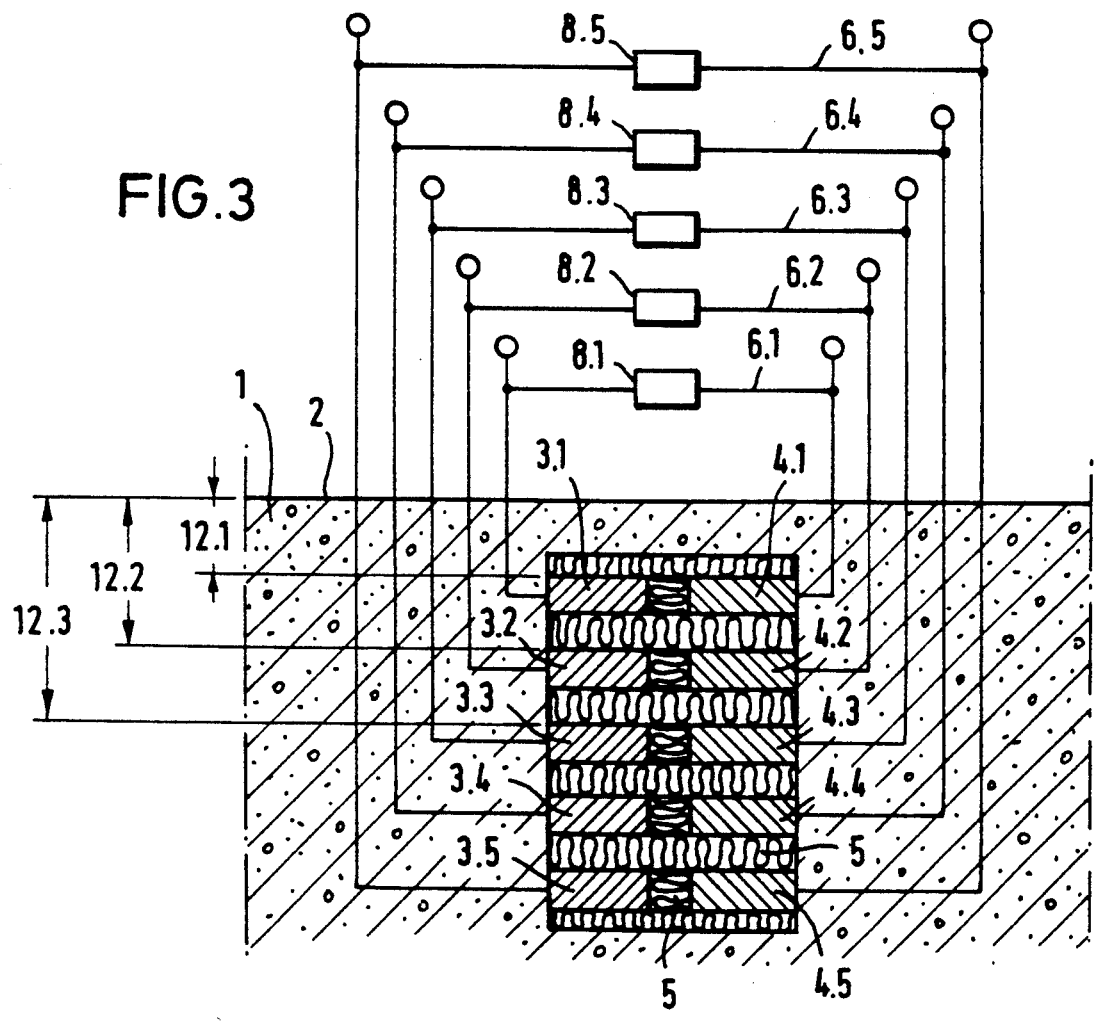
FIG. 3 shows a schematic sectional representation of a second embodiment of the invention.

The principle of the corrosion measuring cells according to the invention will now be described more closely in FIG. 1 using a single measuring cell of the type used in the embodiment according to FIG. 3.

In a concrete structural part 1 which is to be monitored, a cathode electrode 3 made of special steel and an anode electrode made of conventional reinforcing steel are embedded at a lateral distance from one another and at a distance 12 from the upper or external surface 2 of the concrete of the concrete structural part 1. In the case represented; the two electrodes are separated from one another by an insulating piece 5 made of electrically insulating material, but mechanically rigidly connected by the latter, being affixed to this insulating piece 5 so that together with it they form a one-piece probe element. The insulating piece 5 at the same time establishes a predetermined spacing between the anode electrode 4 and the cathode electrode 3.

To each of the two electrodes 3 and 4 an electrical conductor 6 is connected, which conductors run, electrically insulated, through the concrete to the exterior. These conductors connect the electrodes 3 and 4 to one another outside the external surface 2 of the concrete. A measuring device 7 is connected to this electrical connection and can detect a flow of current between the two electrodes 3 and 4.

The electrodes can have any shape, but the size of their contact surfaces with the concrete determines the size of the characteristic current strength for the degree of corrosion. The individual measuring cell, which consists of anode and cathode, is not electrically connected to the conventional reinforcement of the concrete structural part nor with steel structural parts which are embedded in this concrete structural part.

Provided the individual measuring cell formed by the electrodes 3 and 4 lies in a region of concrete in which the alkalinity of the concrete offers the reinforcement protection against corrosion, both the cathode electrode 3 and the anode electrode 4 are covered with an oxide layer and protected by this against corrosion. In this case, no current flows in the electric circuit and no current is measured in the measuring device 7 either. This means that, at the depth or in the zone where the probe element is, no danger of corrosion exists for the reinforcement arranged there.

If, however, the concrete is carbonatized from the outside or if chlorides dissolved in water penetrate from the external surface 2 of the concrete into the inside of the concrete structural part 1, the oxide layer, which covers the anode electrode 4 made of reinforcing steel, is destroyed as soon as the carbonatization of the concrete or the chloride content at this point exceeds a critical limit value. The protection against corrosion of the anode electrode is thus lost. The cathode electrode 3 made of special steel, as a result of its chemical composition is not however subject to corrosion.

When the now unprotected anode electrode, which is now exposed to the action of chlorides for example, begins to corrode, it forms together with the cathode electrode 3 made of special steel a galvanic element, which is connected electrolytically via the concrete and electrically by means of the electrical conductors 6 outside the concrete via the measuring device 7. The electrical current produced as a result of the corrosion can be measured in the measuring device 7. It is a measure of when a danger of corrosion exists at the distance 12 from the external surface 2 of the concrete for the reinforcement there or other steel parts.

The absolute value of the current also gives, taking into consideration the size of the contact surfaces of the electrodes with the concrete, information regarding the rates or speeds of corrosion to be expected, which depend on many influencing variables and without such measurement are difficult to estimate. With the measurement method described, quantitative information regarding the expected rates of corrosion on the reinforcement can thus be obtained.

A design of a corrosion measuring cell according to the invention is represented in FIG. 2.

As can be seen from the drawing, a cathode electrode 3 and an anode electrode 4.1 are arranged in a concrete structural part 1 at a distance 12.1 from the external surface 2 of the concrete. The cathode electrode 3 in the exemplary embodiment represented consists of special steel, but may also consist of copper or another metal which is more noble than structural steel. The anode electrode 4.1 consists of the same material as the reinforcement embedded in the concrete structural part, namely structural steel. It is arranged at a lateral distance from the cathode electrode 3 and like the latter is connected to an electrical conducting wire 6, which is electrically insulated from the concrete and run to the outside. The conducting wires 6 and 6.1 coming from the electrodes 3 and 4.1 are, as explained more closely above in FIG. 1, connected to one another via a measuring instrument 7.1. Furthermore, a low-impedance resistor 8.1 of approximately 10 $\Omega$ is built into the electric circuit, so that the flow of current can at any time be determined by measuring the voltage drop with the measuring device 7.1, without having to interfere with the electric circuit and without having to keep a voltage measuring device ready at this point. Measurement of the current or of the indication of corrosion can be carried out in any manner by means of suitable electrical circuits.

In addition to the first anode electrode 4.1, further anode electrodes 4.2, 4.3, 4.4, 4.5 are arranged at a lateral distance from one another and at different depths, that is to say at ever larger distances 12.2, 12.3, 12.4 and 12.5 from the external surface 2 of the concrete. Like the first anode electrode 4.1, the further anode electrodes 4.2, 4.3, 4.4, 4.5 are connected to electrical conductors 6 6.3, 6.4 and 6.5, which are, electrically insulated, run through the concrete to the outside and in each case, by means of their own measuring instruments 7.2, 7.3 etc., connected to the electrical conductor 6, which is connected to the cathode electrode 3. In each of the individual electric circuits, as described above, low-impedance resistors 8.2, 8.3, 8.4 and 8.5 are also connected.

It can be seen that, with advancing penetration of carbonatization or of aqueous chloride solutions from the external surface 2 of the concrete into the inside of the concrete structural part 1, one anode electrode after another will be reached by the carbonatization or the chlorides and they will begin to corrode at a corresponding temporal separation from one another and to produce a current, which can be established on the respective assigned measuring devices 7.1 to 7.5 and measured according to size. It is thus possible to detect the temporal course of the penetration of substances which are capable of damaging the reinforcement, and it is possible to take measures at the right time in order to stop the destruction in good time.

A further embodiment of the invention is shown in FIG. 3. In this embodiment, the anode electrodes made of reinforcing steel 4.1 to 4.5 are connected mechanically to respective cathodes 3.1 to 3.5 by means of intermediate insulating pieces 5 to form one-piece probe elements. These probe elements are insulated from one another by means of suitable insulating layers 5' and joined together into a plate-shaped cell element, which can be embedded as a unit in the concrete structural part. In this connection, the pairs of electrodes of the individual probe elements are connected to one another via electric circuits 6.1 to 6.5, which are separate from one another, via measuring instruments 7.1 to 7.5, which are here not shown in greater detail, low-impedance resistors 8 being provided in this case also.

In the same way as in the exemplary embodiment described above, the corrosion currents caused by corrosion, which arise at the different depths 12.1 to 12.5 at which the probe elements are situated, can be detected by the respective measuring instruments, it being possible in each case to establish the time at which the corrosion begins at the corresponding depth and also to determine the strength of the respective corrosion currents, which occurs in the individual layers to which the respective probe elements are assigned.

In the exemplary embodiments of the invention represented in FIGS. 4 to 8, the probe 15 consists of four probe elements 16 of the type more closely described in FIG. 1, that is to say each probe element is composed of a cathode electrode 3 made of special steel and an anode electrode 4 made of reinforcing steel, which are connected to one another by means of an insulating piece 5 made of electrically non-conductive material to be mutually electrically insulated. The individual probe elements are fastened, parallel and at a mutual distance from one another, with their two outer ends 16a and 16b to lateral shafts 17 and 18, which consist of an electrically nonconductive insulating material, for example a suitable plastic, and in the exemplary embodiment represented in FIG. 4 have a rectangular cross section. To each of the electrodes 3 and 4, one electrical conducting wire 6 is connected, which can be electrically conductively connected to the fastening means, for example a rivet or a screw 19, which mechanically rigidly connects the respective electrode 3 or 4 to the assigned shaft 17 or 18. The electrical wires 6 of each one of the pairs of electrodes or of a probe element 16 are run to the external side 2 of the concrete of the concrete member 1 and also, as indicated in FIG. 2, each connected to a measuring device 7, it being possible also to connect a measurement resistor 8 in the respective electric circuit. These measuring devices and measurement resistors are, however, not shown in FIGS. 4 to 7.

As can be seen from FIG. 5, the probe 15, in which five probe elements 16 and the lateral shafts 17 and 18 are rigidly connected to one another to form a single component, is embedded in the concrete structural part 1 with a slight inclination in relation to the surface 2 of the concrete in such a manner that the electrodes run approximately parallel to the surface 2 of the concrete and are at different distances 12.1, 12.2, 12.3 and 12.4 from the latter. At the same time the arrangement is such that the probe elements are at the same distance from one another as the uppermost probe element is from the external surface 2 of the concrete.

The probe represented in FIGS. 6 and 7 corresponds essentially to the probe according to FIGS. 4 and 5. The difference is only that each shaft 17 or 18 has at least one cavity 20, which runs in the longitudinal direction of the shaft and in which the conductors 6, which are connected to the electrodes 3 and 4 of the probe elements 16, are accommodated. The shafts can have a hollow profile, for example a box profile, as shown on the left of FIGS. 6 and 7, but they may instead have a U-shaped profile, as shown on the right of FIGS. 6 and 7.

Figure 8:
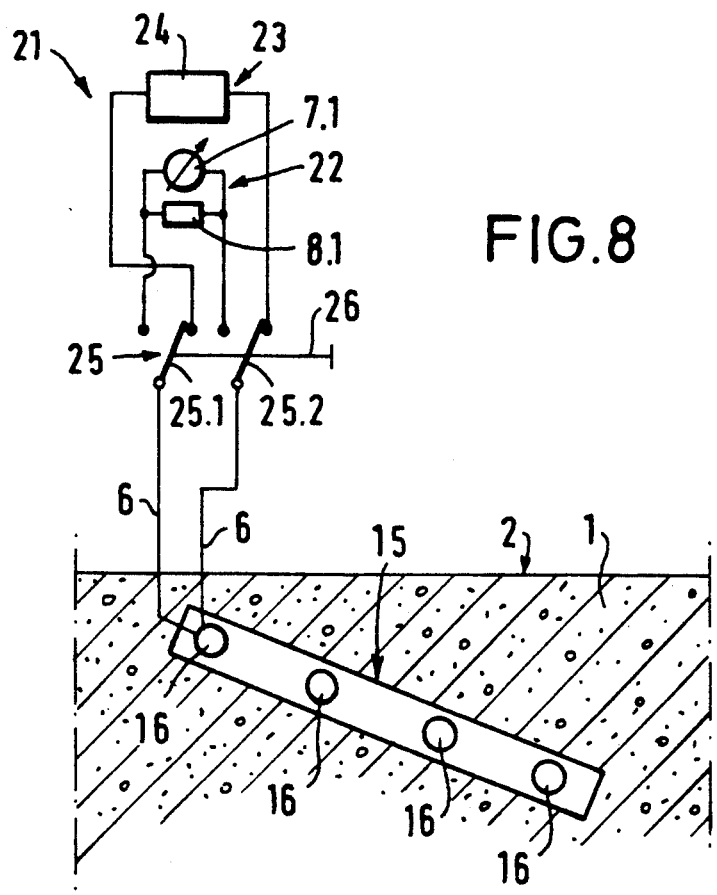
FIG. 8 shows a corrosion measuring cell embodying the invention with a component as represented in FIG. 5 or 6 and polarizing circuits for the individual pairs of electrodes, of which, however, only one circuit is shown in FIG. 8.

In the embodiment according to FIG. 8, the probe 15 is, like the embodiments described above, designed in the manner of a rung ladder and is again embedded in the concrete structural part 1 with a gentle inclination towards the external surface 2 of the concrete. Of the electrical conductors which are run to the outside and connected to the individual probe elements, only those electrical conducting wires 6 are represented which are assigned to the uppermost probe element. The remaining probe elements, which are arranged deeper in the concrete, have simple measuring elements, as represented in FIGS. 1 and 2, but they may instead have the same measurement circuit 21 as the uppermost probe element 16.

The measurement circuit 21, which is assigned to the uppermost probe element 16, has a measuring device 22 which consists, as does the exemplary embodiment shown in FIG. 2, of a measuring element 7.1 and a low-impedance resistor 8.1. The measuring device 22 is connected in parallel to a polarizing device 23, which has a potentiostat 24. By means of a selective switch 25 with two contact studs 25.1 and 25.2, the electrical conductors 6 coming from the probe element 16 can be optionally switched over, either manually or using a suitable drive 26, from the measuring device 22 to the polarizing device 23 and vice-versa. It is thus possible, after the start of corrosion of the anode electrode of the probe element 16, to measure the corrosion current with the measuring device 22, but after measurement to connect the electrical conductors 6 to the polarizing device 23. The potentiostat 24 of the polarizing device 23 then polarizes the anode electrode made of reinforcing steel in such a manner that the corrosion current and thus the corrosion stops on the probe element to which the measurement circuit 21 is connected. If at a later stage the respective current state and the existing danger of corrosion are to be inspected again, the measuring device 22 can once again be connected to the electrical conductors 6 of the probe element by means of switching of the selective switch 25, in order to establish the corrosion current and thus the degree of corrosion present at the time.

The invention is not limited to the represented exemplary embodiments; various modifications and additions are possible without going beyond the scope of the invention. For example, the measurement circuit shown in FIG. 8 can also be used in corrosion measuring cells as represented in FIGS. 2 and 3. Moreover, a different polarizing circuit can also be used for the probe elements.

Figure 9:
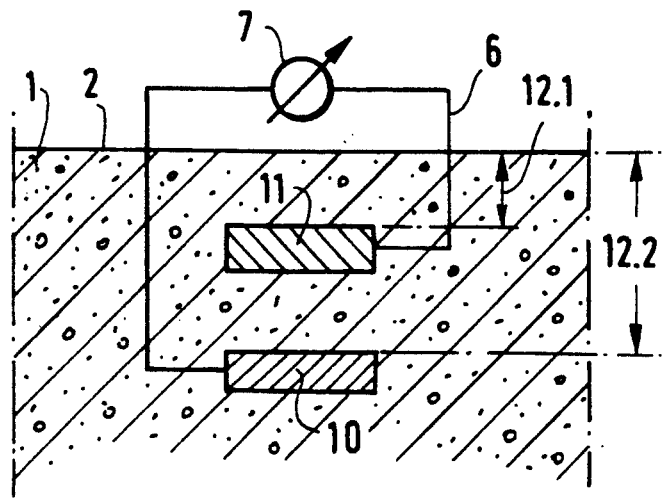
FIG. 9 shows a schematic representation of a corrosion measuring cell embodying the invention, in which both the anode electrode and the cathode electrode consist of conventional structural steel.

The corrosion measuring cell may in some cases be designed in such a manner that not only the anode electrode, but also the cathode electrode, is manufactured from reinforcing steel. Then, in relation to the external surface 2 of the concrete, the cathode is deeper in the concrete structural part 1 than the anode electrodes. Such an embodiment is schematically represented in FIG. 9. When the anode electrode 11 in such an embodiment is reached by carbonatization or by chlorides which penetrate from the external surface 2 of the concrete into the inside of the concrete structural part 1, the oxide layer surrounding the anode electrode is destroyed. However the cathode electrode 10, which lies deeper and to which the chlorides etc. have not yet penetrated, still has protection against corrosion. The deeper electrode 10 then works automatically as cathode, while the higher electrode 11 works as anode. This embodiment of the corrosion measuring cell has the disadvantage, however, that it can no longer work when the protection against corrosion of the deeper electrode 10 is also lost.

Figure 10:
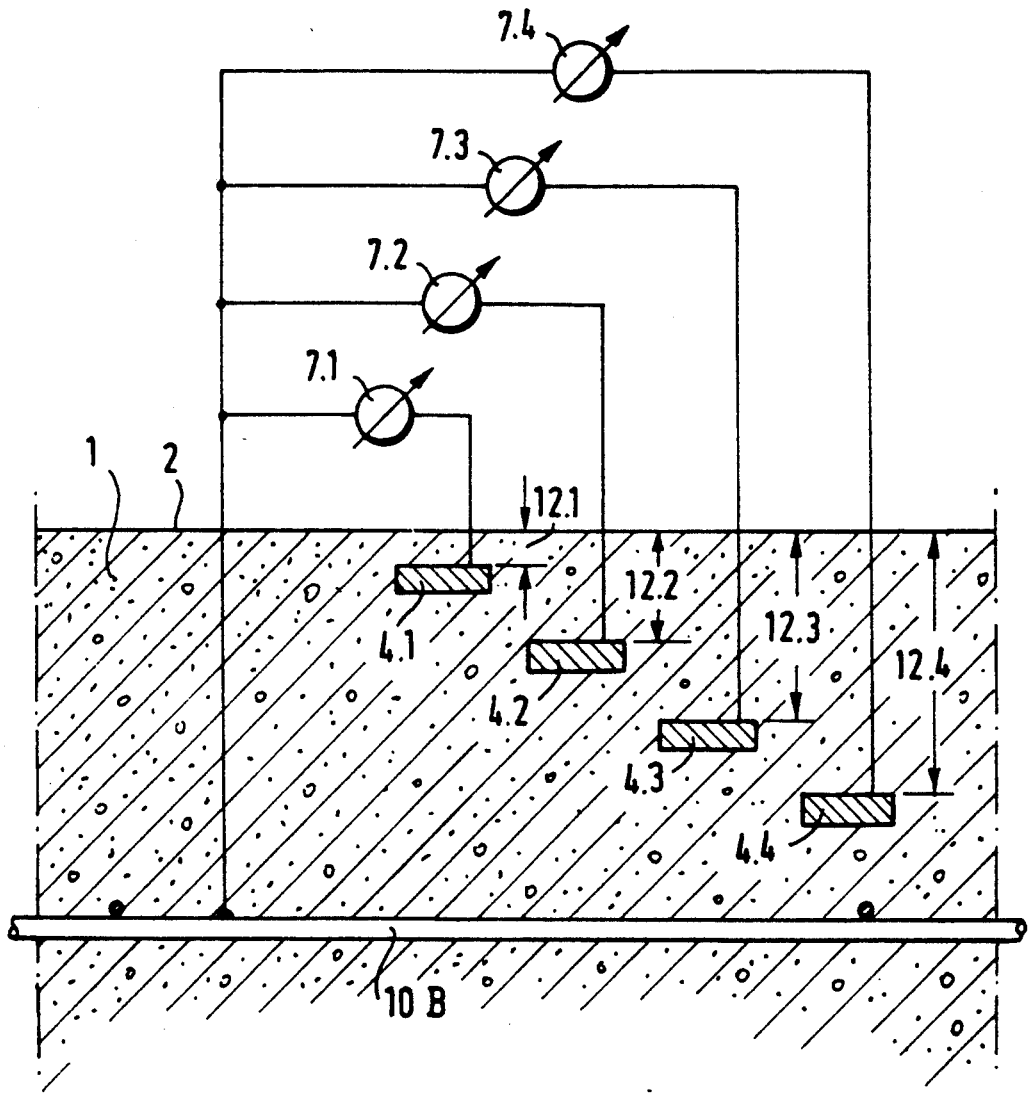
FIG. 10 shows a schematic sectional representation of a corrosion measuring cell embodying the invention, built into a reinforced concrete structural part according to the principle in FIG. 9.

The deeper electrode 10, which works as cathode, may be a structural steel reinforcement which is embedded in the concrete and is to be monitored. This means that the anode electrode 11 or several anode electrodes arranged at different depths are shortcircuited with the structural steel reinforcement via the measuring instrument 7, so that no separate cathode electrodes have to be built in. Such an embodiment is shown in FIG. 10.

In the claims, "conventional steel" means steel of a type used for reinforcement or structural purposes. "Corrosion resistant" means resistant to corrosion in concrete that is carbonati sed and/or contains chloride.

What is claimed is:

1. A corrosion measuring cell for structural or reinforcing steel embedded in a concrete part having an exterior surface, the cell comprising:
   at least one cathode electrode embedded in the concrete part, said at least one cathode electrode being of corrosion-resistant metal;
   a plurality of spaced anode electrodes of conventional steel embedded in the concrete part, said anode electrodes being spaced from said at least one cathode electrode and spaced from one another in such manner that the spaced anode electrodes are situated at varying depths from said concrete exterior surface;
at least one current measuring element, at said concrete exterior surface;
electrical connections extending from each of said at least one cathode electrode and each of said anode electrode of said current measuring element such that each of said anode electrodes is connectable through at least one of said at least one current measuring element to said cathode electrode, for detection/measurement of current due to corrosion at any one of said spaced anode electrodes.

2. A corrosion measuring cell as set forth in claim 1 comprising a respective said cathode electrode for each of said anode electrodes, each such pair of electrodes being spaced at a different distance from the concrete exterior surface and having a respective said measuring element.

3. A corrosion measuring cell as set forth in claim 2 comprising a plurality of one-piece spaced probe elements, each probe element comprising one of said anode electrodes, its corresponding said cathode electrode, and an insulating piece between said anode and cathode electrodes joining them together to form a one-piece structure.

4. A corrosion measuring cell as set forth in claim 3 comprising a pair of insulating shafts wherebetween said spaced probe elements are rungwise disposed.

5. a corrosion measuring cell as set forth in claim 4 wherein each shaft has a longitudinal cavity for receiving the electrical connections to said at least one measuring element.

6. A corrosion measuring cell as set forth in claim 4 wherein the shafts are built into the concrete part with a slight inclination to the exterior surface thereof to provide the varying depths of the anode electrodes, the probe elements extending substantially parallel to the exterior surface.

7. A corrosion measuring cell as set forth in claim 1 comprising an insulating shaft, the anode electrodes being mounted spaced along said shaft.

8. A corrosion measuring cell as set forth in claim 1, comprising a polarising device for a plurality of said anode electrodes thereof, said polarising device comprising means switchable to polarise said anode electrode so as to stop corrosion current and hence corrosion thereof.

9. A corrosion measuring cell as set forth in claim 8 wherein the polarising device is connected in parallel with the measuring element for said anode electrode, and comprising a switch for switching connection of the anode electrode between connections through the measuring element to the cathode electrode and connection through the polarising device to the cathode electrode.

10. A corrosion measuring cell as set forth in claim 8 wherein the polarising device comprises a potentiostat.

11. A corrosion measuring cell as set forth in claim 8 wherein each of said anode electrodes is connected to such a polarising device.

12. A corrosion measuring cell for structural or reinforcing steel embedded in a concrete part having an exterior surface, the cell comprising:
a plurality of anode electrodes of conventional steel embedded in the concrete part;
at least one cathode electrode also of conventional steel, embedded in the concrete part spaced from said anode electrodes and at a substantially greater depth from the exterior surface than said anode electrodes;
at least one current measuring element accessible at the concrete exterior surface, and
electrical connections extending from each cathode electrode and each anode electrode to a said current measuring element, whereby each said anode electrode is connectable through said current measuring element to said cathode electrode at a greater depth, for detection/measurement of current due to corrosion occurring at each said anode electrode.

13. A corrosion measuring cell as set forth in claim 12 wherein said plurality of said anode electrodes spaced from one another at varying depths from the concrete exterior surface.

14. A corrosion measuring cell as set forth in claim 13 comprising a respective said current measuring element for each of said anode electrodes.

15. A corrosion measuring cell as set forth in claim 13 comprising a single cathode electrode for said plurality of anode electrodes.

16. A corrosion measuring cell as set forth in claim 12, comprising a polarizing device for a plurality of said electrodes thereof, said polarizing device comprising means switchable to polarize said anode electrode so as to stop corrosion current and hence corrosion thereof.

17. A corrosion measuring cell for monitoring the prospect of corrosion to a steel part embedded in a concrete part having an exterior surface, comprising:
a plurality of electrodes of conventional steel embedded in the concrete part at a position between the steel part and the exterior surface;
at least one current measuring element accessible at the concrete exterior surface, and
electrical connections extending from the steel part and from each of said anode electrodes to a said current measuring element whereby each of said anode electrodes is connectable to the steel part through a said current measuring element, for detection/measurement of current due to corrosion occurring at said anode electrode with said steel part functioning as a cathode electrode.

18. A corrosion measuring cell as set forth in claim 17 wherein said plurality of said anode electrodes spaced from one another at varying depths between the exterior surface and said steel part.

19. A corrosion measuring cell as set forth in claim 18 comprising a respective said current measuring element for each of said anode electrodes.

20. A corrosion measuring cell as defined in claim 17, wherein said steel part is a structural steep part.

21. A corrosion measuring cell as defined in claim 17, wherein said steel part is a reinforcing steel part.

22. A corrosion measuring cell as set forth in claim 17, comprising a polarizing device for a plurality of said electrodes thereof, said polarizing device comprising means switchable to polarize said anode electrode so as to stop corrosion current and hence corrosion thereof.

23. A probe system for incorporation into a concrete part having an exterior surface, for monitoring the prospect of corrosion to structural or reinforcing steel embedded in the concrete part, the probe comprising:
at least one insulating shaft;
a plurality of anode electrodes of conventional steel, said anode electrodes being spaced from one another along the shaft;

at least one cathode electrode of corrosion-resistant material, mounted on the shaft;
at least one current measuring element;
electrical connections extending from each anode electrode and from each cathode electrode to a said current measuring element whereby each anode electrode is connectable through said current measuring element to said cathode electrode, for detection/measurement of current due to corrosion at any one of said anode electrodes.

24. A probe system as set forth in claim 23 comprising a respective said cathode electrode for each of said anode electrode.

25. A probe system as set forth in claim 24 comprising a plurality of one-piece probe elements, each of said probe elements comprising one of said anode electrodes, its corresponding cathode electrode, and an insulating piece, said insulating piece joining between the anode electrode and cathode electrode of the probe element.

26. A probe system as set forth in claim 25 comprising two insulating shafts extending side by side, said probe elements extending between the shafts at positions spaced along them.

27. A probe system as set forth in claim 23 wherein the electrical connections extend along a said insulating shaft.

28. A corrosion measuring cell as set forth in claim 23, comprising a polarizing device for a plurality of said electrodes thereof, said polarizing device comprising means switchable to polarize said anode electrode so as to stop corrosion current and hence corrosion thereof.

* * * * *